(12) United States Patent
Kück et al.

(10) Patent No.: US 9,039,613 B2
(45) Date of Patent: May 26, 2015

(54) BELT WITH SENSORS

(75) Inventors: Kai Kück, Hamburg (DE); Cornelia Schrader, Lübeck (DE); Steffen Schmitt, Tremsbüttel (DE); Hans-Ullrich Hansmann, Barnitz (DE)

(73) Assignee: Dräger Medical GmbH, Lübeck (DE)

( * ) Notice: Subject to any disclaimer, the term of this patent is extended or adjusted under 35 U.S.C. 154(b) by 1574 days.

(21) Appl. No.: 12/369,963

(22) Filed: Feb. 12, 2009

(65) Prior Publication Data
US 2009/0229039 A1 Sep. 17, 2009

(30) Foreign Application Priority Data
Mar. 11, 2008 (DE) .......... 10 2008 013 707

(51) Int. Cl.
| | |
|---|---|
| A61B 5/00 | (2006.01) |
| A41F 9/00 | (2006.01) |
| A41D 13/12 | (2006.01) |
| A61B 5/01 | (2006.01) |
| A61B 5/0408 | (2006.01) |
| A61B 5/053 | (2006.01) |

(Continued)

(52) U.S. Cl.
CPC .............. *A61B 5/00* (2013.01); *A41D 13/1254* (2013.01); *A41D 13/1281* (2013.01); *A41F 9/00* (2013.01); *A61B 5/01* (2013.01); *A61B 5/0408* (2013.01); *A61B 5/0537* (2013.01); *A61B 5/11* (2013.01); *A61B 5/1455* (2013.01); *A61B 5/6831* (2013.01)

(58) Field of Classification Search
CPC ............... A61B 5/683–5/6831; A61B 5/02055
USPC ......... 600/300–301, 309, 363–365, 372–373, 600/377–379, 382–384, 386–394, 481, 485, 600/500–503, 508, 515–519, 529–531, 600/544–547, 549, 587–595; 28/100–171
See application file for complete search history.

(56) References Cited

U.S. PATENT DOCUMENTS

| | | | | |
|---|---|---|---|---|
| 3,752,163 | A * | 8/1973 | Kaplan | 450/117 |
| 5,336,554 | A * | 8/1994 | Knight | 428/137 |
| 6,069,097 | A * | 5/2000 | Suzuki et al. | 442/328 |

(Continued)

FOREIGN PATENT DOCUMENTS

| EP | 1 054 092 A1 | 11/2000 |
|---|---|---|
| EP | 1598172 A1 * | 11/2005 |

OTHER PUBLICATIONS

Bueche, F. in "Mechanical Properties of Natural and Synthetic Rubbers", Journal of Polymer Science, vol. 25, p. 305-324, 1957.*

*Primary Examiner* — William Thomson
*Assistant Examiner* — Marie Archer
(74) *Attorney, Agent, or Firm* — McGlew and Tuttle, P.C.

(57) ABSTRACT

A stretchable belt (1) provided for medical purposes for use on the body of a patient has at least one sensor (8) for detecting at least one parameter of the patient's body. An adaptation to different body sizes and motions of the patient is provided without separate length adjusting members being necessary or without the need to stock different belt sizes. Furthermore, the belt is able to be manufactured at a low cost and makes possible simple and reliable handling, even for patients. The belt material (1) has at least one material area (2) with a lower spring rate in the longitudinal extension than at least one material area (3) with a higher spring rate of the belt (1).

3 Claims, 4 Drawing Sheets

(51) Int. Cl.
 *A61B 5/11* (2006.01)
 *A61B 5/1455* (2006.01)

(56) References Cited

U.S. PATENT DOCUMENTS

| | | | |
|---|---|---|---|
| 6,342,044 B1* | 1/2002 | Frangi et al. | 602/19 |
| 6,783,506 B2* | 8/2004 | Seering et al. | 602/19 |
| 2002/0132091 A1* | 9/2002 | Worley | 428/138 |
| 2003/0153958 A1 | 8/2003 | Yamazaki et al. | |
| 2003/0208830 A1* | 11/2003 | Marmaropoulos et al. | 2/69 |
| 2005/0020982 A1* | 1/2005 | Shaw | 604/179 |
| 2005/0119701 A1* | 6/2005 | Lauter et al. | 607/2 |
| 2008/0015454 A1 | 1/2008 | Gal | |
| 2008/0287770 A1* | 11/2008 | Kurzweil et al. | 600/388 |
| 2009/0203984 A1* | 8/2009 | Dias et al. | 600/388 |

* cited by examiner

BELT WITH SENSORS

CROSS REFERENCE TO RELATED APPLICATIONS

This application claims the benefit of priority under 35 U.S.C. §119 of German Patent Application DE 10 2008 013 707.3 filed Mar. 11, 2008, the entire contents of which are incorporated herein by reference.

FIELD OF THE INVENTION

The present invention pertains to a stretchable belt for medical purposes for use on a patient's body with at least one sensor for detecting at least one parameter of the patient's body.

BACKGROUND OF THE INVENTION

It is necessary for various medical applications to place belts with sensors on the body of patients in order to measure, e.g., ECG or the temperature of the patient. The belts are often used as chest belts. The belts will be in contact with the body with a certain tensile force, and a certain lower tensile force is necessary to guarantee reliable contact of the belt, on the one hand, and, on the other hand, a certain upper tensile force shall not be exceeded to guarantee comfort.

It is necessary for this reason to keep in stock belts in various sizes, which are adapted to the patients' body sizes. However, this requires a costly effort in manufacture, storage and stocking. In addition, the patients must disadvantageously try on different belts—similarly to pieces of clothing in different sizes—until one belt will have the right size. Moreover, it is known that the length of the belts can be made adjustable by means of Velcro fasteners, buttons, hooks/eyelets, buckles or loops. As a result, an adjustable length of the belt is utilized and a residual length of the belt remains unused as an overhang on the belt. The overhang remains disturbingly on the belt and may cause potential pressure points because of the outer clothing. It is, in general, not possible to remove the overhang because of electric lines or other means for detecting the parameters of the patient's body. Hooks, eyelets, buttonholes, Velcro fasteners and Velcro hooks need to be arranged in rows, so that unused rows remain in order to make adjustability possible. The unused rows represent possibilities of error, require a greater effort and may lead to disturbances, especially pressure points with the outer clothing. Adjustability by means of buckles and loops, as, for example, in the case of backpack straps, requires some skill in order to obtain the desired length. Furthermore, the belt is present in three layers in the loop, i.e., pressure points will, in general, develop on the loop. The closure and the length adjusting member often form one unit in belts, so that the length of the belt must disadvantageously be reset after opening the belt.

US 2003/0153958 A1 shows a belt of this class with electrodes for applying to the body surface stimulating pulsating current in the frequency range of, for example, 20 Hz to 50 Hz as well as for measuring the impedance of the body. The belt consists of synthetic fibers containing 18% Nylon and 18% urethane, so that simple adaptation to different body sizes is not possible.

SUMMARY OF THE INVENTION

An object of the present invention is therefore to provide a belt in which the adaptation to different body sizes and motions of the patients is brought about in a simple manner without separate length adjusting members being necessary or without stocking of different belt sizes being required. Furthermore, the belt will be able to be manufactured at a low cost and make possible reliable handling, even for patients.

This object is accomplished with a stretchable belt for medical purposes for use on the body of a patient, with at least one sensor for detecting at least one parameter of the patient's body, wherein the belt has, in the longitudinal extension, at least one area with a lower spring rate than at least one area of the belt that has a higher spring rate. Different spring rates of the belt in the longitudinal extension of the belt make it possible to easily adapt the belt to different body sizes of patients.

In another embodiment, the longitudinal extension of the at least one area with the lower and/or higher spring rate equals at least 0.5 cm and especially at least 1 cm.

Advantageously, the at least one area with the lower spring rate is embodied by means of at least one perforation of the belt.

In an additional embodiment, the at least one area with the lower spring rate can be deactivated by means of a blocking means. The average spring rate of the belt can thus be better adapted to different body sizes.

In particular, the at least one area with the lower spring rate can be activated by removing the blocking means.

In another variant, the blocking means is a tape, especially an adhesive tape, and/or a thread.

The at least one perforation can be preferably widened in order to obtain a lower spring rate of the at least one area with perforation. Widening of the perforation makes it possible to lower the average spring rate.

In an additional embodiment, a perforation can be made on the belt in order to obtain the area with the lower spring rate.

The average spring rate of the at least one area with the lower spring rate differs especially by at least 10% and especially at least 20% from the average spring rate of the at least one area with the higher spring rate.

The belt preferably has at least two, especially at least five areas with a lower and/or higher spring rate.

In a stretchable belt according to the present invention for medical purposes for use on the body of a patient, with at least one sensor for detecting at least one parameter of the patient's body, a longitudinal stretching of the belt by 3% requires a tensile force of less than 7 N, especially less than 3 N. Thus, weak forces occur during a great change in the length of the belt, so that the belt can be easily adapted to different body sizes.

In an additional embodiment, a longitudinal stretching of the belt by 3% requires a force of between 2.5 N and 3.5 N.

In a stretchable belt according to the present invention for medical purposes for use on the body of a patient, with at least one sensor for detecting at least one parameter of the patient's body, the belt contains micropores, which are stretchable during the longitudinal stretching of the belt, preferably in the longitudinal direction. The micropores thus reduce the average spring rate of the belt, i.e., the belt can be easily adapted to different body sizes. Moreover, the micropores act as a kind of perforation, because the micropores also interrupt the material, of which the belt consists.

In a preferred embodiment, the maximum extension, especially the diameter, of the micropores is less than 30% and especially less than 10% of the thickness of the belt. The maximum extension, e.g., the diameter, is, for example, in the range of 0.01 mm to 50 mm and especially between 0.1 mm and 3 mm. The micropores may have different shapes in the unstretched or stretched state, e.g., the shape of a sphere, hemisphere, torus, cuboid, cube, cylinder, cone, octahedron, parallelepiped or ellipsoid of revolution.

In a stretchable belt according to the present invention for medical purposes for use on the body of a patient, with at least one sensor for detecting at least one parameter of the patient's body, the volume of the belt increases during a longitudinal stretching of the belt. Thus, the volume increase brought about by the increase in the length of the belt is greater in case of a longitudinal stretching of the belt than the reduction of the volume of the belt that is brought about by a reduction of the cross-sectional area.

In particular, the volume of the belt increases by at least 0.3% and especially by at least 0.5% to 3% in case of a longitudinal stretching of the belt by 3%.

In one variant, the belt consists at least partly of neoprene and/or composite materials and/or foamed vulcanized materials and/or composites with textiles. Composite materials consist of different materials and are preferably built up in different layers. These are materials or substances with a low spring rate, i.e., high elasticity, so that the belt can be easily adapted to different body sizes with low tensile forces developing in the belt.

The belt preferably comprises at least one fastening means for the at least one sensor.

In another embodiment, the at least one sensor is at least one electrode for detecting electrocardiogram (ECG) and/or electroencephalogram (EEG) and/or electromyogram (EMG) and/or at least one acceleration sensor and/or at least one temperature sensor and/or at least one ring-shaped coil line in a belt for impedance measurement and/or at least one sensor for measuring the oxygen saturation in the blood.

In another variant, the belt has a circumference or length in the range of 0.1 m to 1.2 m in the unstretched state.

The belt advantageously has at least one means for fastening at least one sensor.

Two exemplary embodiments of the present invention will be described in more detail below with reference to the attached drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiments of the invention are illustrated.

DESCRIPTION OF THE PREFERRED EMBODIMENTS

Figure 1:
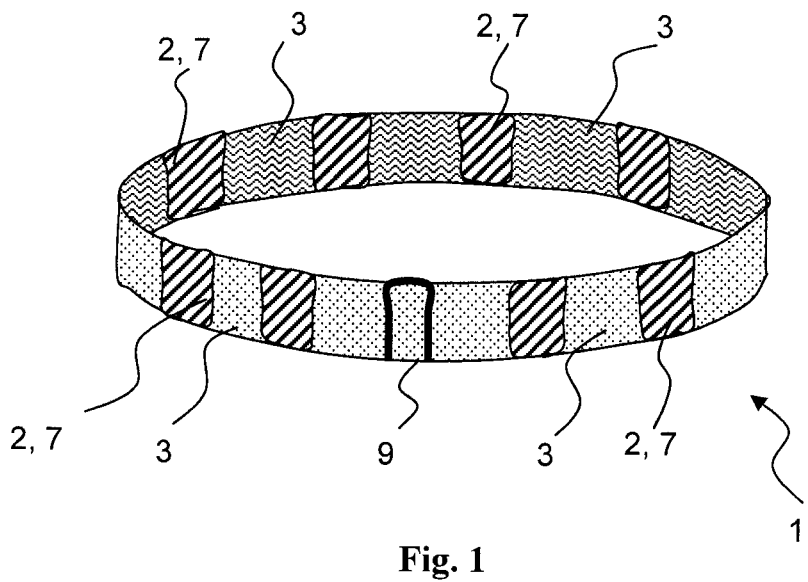
FIG. 1 is a perspective view of a belt in an unstretched state in a first exemplary embodiment according to the invention.
Figure 2:
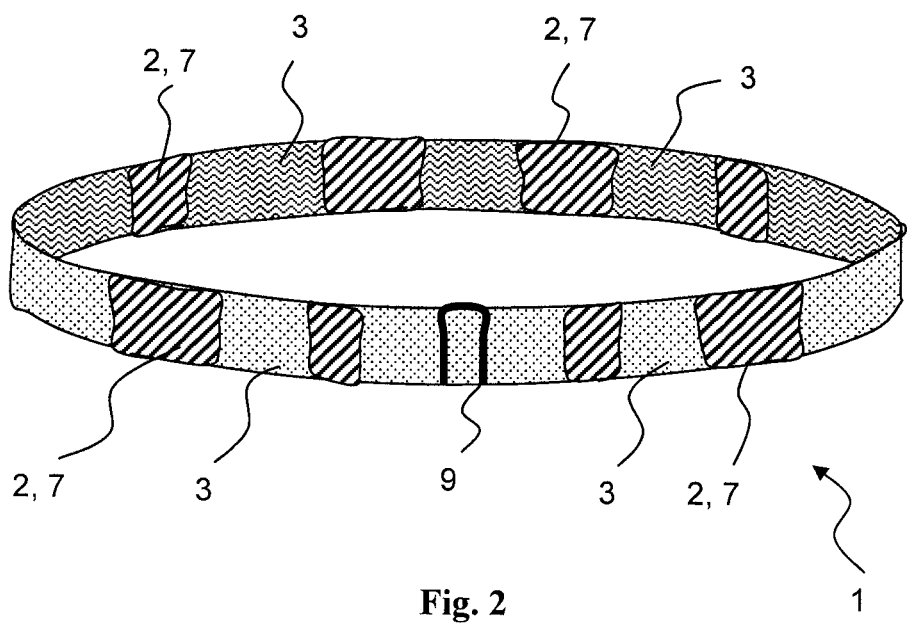
FIG. 2 is a perspective view of the belt according to FIG. 1 in a stretched state.
Figure 3:
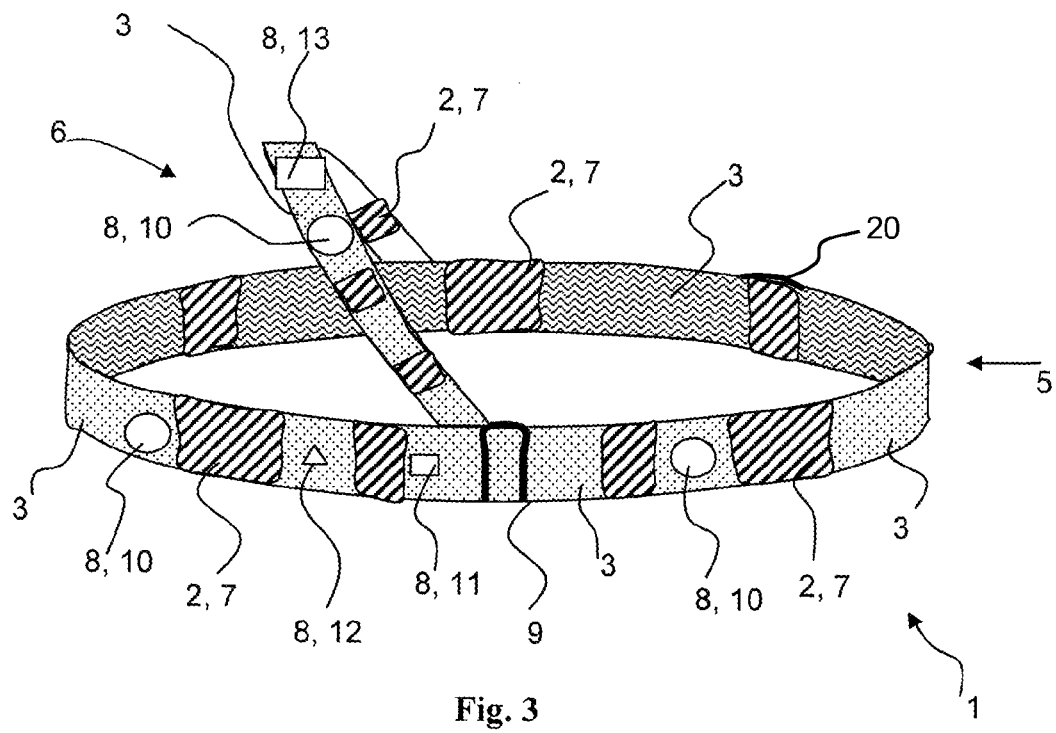
FIG. 3 is a perspective view of a belt in an unstretched state in a second exemplary embodiment according to the invention.
Figure 4A:
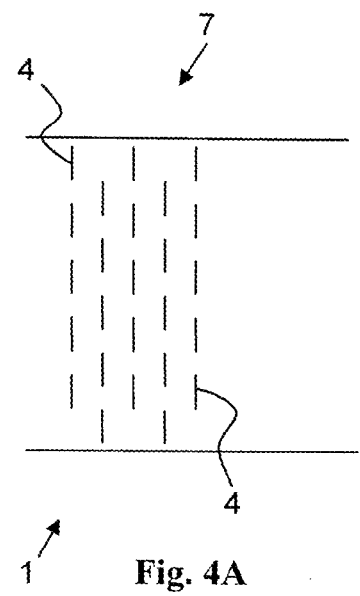
FIG. 4A is a top view of a first embodiment of a stretching zone in an unstretched state.
Figure 4B:
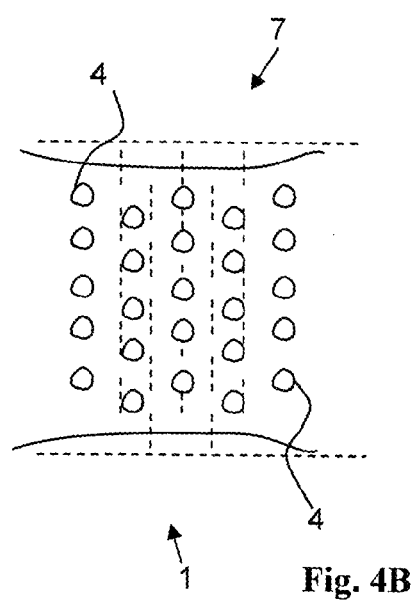
FIG. 4B is a top view of the first embodiment of a stretching zone in a stretched state.
Figures 5A, 5B:
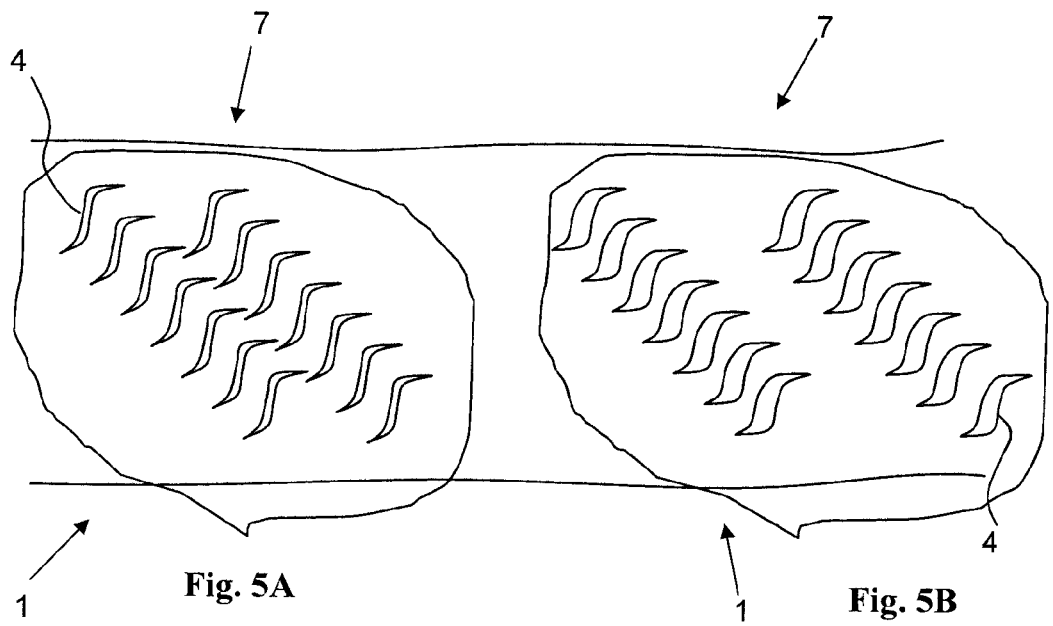
FIG. 5A is a top view of a second embodiment of a stretching zone in an unstretched state.
FIG. 5B is a top view of the second embodiment of a stretching zone in a stretched state.
Figures 6A, 6B:
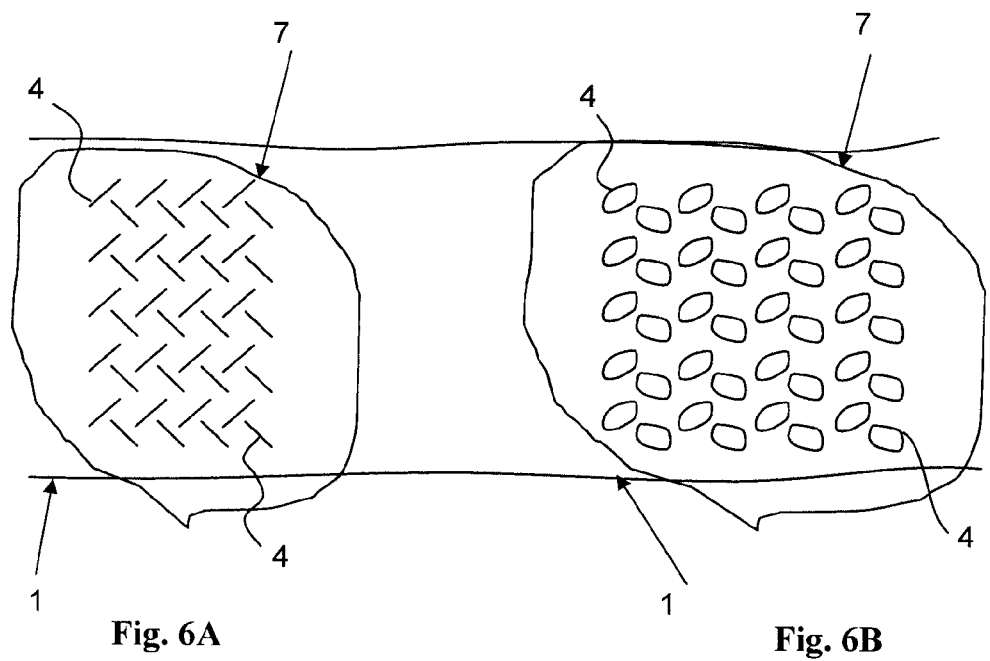
FIG. 6A is a top view of a third embodiment of a stretching zone in an unstretched state.
FIG. 6B is a top view of the third embodiment of a stretching zone in a stretched state.

Referring to the drawings in particular, FIGS. 1, 2 and 3 show a belt 1 according to the present invention for detecting at least one parameter of the patient's body, e.g., ECG values or temperature. Belt 1 can be opened and closed by means of a closure 9. The belt 1 is used, for example, in hospitals. Sensors for detecting at least one parameter of the body of a patient are not shown in the exemplary embodiment shown in FIGS. 1 and 2.

The belt 1 consists of elastic neoprene with micropores as a foamed vulcanized material, which is laminated on both sides. Belt 1 has a thickness of 1.5 mm, a width of 10 cm and a length of 75 cm in the unstretched state (FIGS. 1 and 3). The belt 1 shown in FIG. 3 in the second exemplary embodiment additionally has a shoulder strap 6, which supports reliable seating and acts at the same time as a carrier for sensors 8. Thus, the belt 1 in the second exemplary embodiment consists of a chest belt 5 and the shoulder strap 6. Electrodes 10 for ECG measurement, an acceleration sensor 11, a line or electric coil incorporated in the chest belt 5 for measuring the impedance (not shown) and a temperature sensor 12 are incorporated as sensors 8 in the chest belt 5 or are connected to the chest belt 5 by a fastener for fastening the sensor to the belt material. The shoulder strap 6 has an electrode 10 for the ECG measurement and an $SpO_2$ sensor 13 for measuring the oxygen saturation or a means for fastening an $SpO_2$ sensor 13.

Elastic materials require a tensile force F during a change in length or stretching s. The tensile force F can be calculated essentially with the physical model of Hooke's law, according to which the tensile force F is the product of a spring rate c by the change in length s. The higher the spring rate c as a proportionality constant, the stronger is the force for a certain change in the length of the belt 1. The spring rate c will be as low as possible in order to obtain a tensile force that is present for the patient, for example, in the range of 2 N to 4 N (Newton), even in case of great stretching of the belt 1. Neoprene has a low spring rate c, so that the belt 1 requires only slightly increasing forces to be applied at the patient, because of the tensile force in the belt 1 even in case of greater changes in length.

The belt 1 according to the first exemplary embodiment or the chest belt 5 according to the second exemplary embodiment has eight or seven areas 2, respectively, with a lower spring rate c as stretching zones 7 than the other areas 3 with a higher spring rate c. The shoulder strap 6 has three stretching zones 7. The eight and seven stretching zones 7 as areas 2 with a lower spring rate are obtained by means of a perforation 4 of the belt. FIGS. 4A through 6B show three possible embodiments of perforations 4. The perforations 4 are designed in FIGS. 4A and 4B in the unstretched state of the belt 1 (shown in FIG. 4B) as slots with a length of about 1.2 cm, which are directed at right angles to the longitudinal axis of the belt 1. In the stretched state, shown in FIG. 4B, the perforations 4 have an approximately circular or elliptical shape. In the second embodiment of perforation 4 (FIGS. 5A, 5B), the perforations 4 have an S-shaped or serpentine course, and the perforations 4 have a larger opening in the stretched state, shown in FIG. 5B. In the third embodiment of the perforations 4 shown in FIGS. 6A, 6B, these are designed in the unstretched state (shown in FIG. 6A) as slots with a length of approx. 1.2 cm, which are directed at an angle of approx. +45° and −45° to a longitudinal axis of the belt 1.

The stretching zones 7 are fixed in the new state of the belt 1 by means of an adhering adhesive tape acting as a blocking means 20 (shown in FIG. 3), which is not stretchable or is stretchable only slightly, so that the stretching zones 7 cannot be stretched when a force acts on the belt 1. It is also possible to use a tape, which is fastened to the belt 1 by means of positive-locking connection, e.g., Velcro hooks, as a blocking means to deactivate the stretching zones 7. Instead of an adhesive tape, it is also possible to use as the blocking means 20, for example, a thread incorporated in belt 1, which thread is to be cut to activate the stretching zones 7 (not shown). Moreover, the perforations 7 may be designed as incomplete perforations 7 in the new state, which are additionally torn up in case of the release or activation of a stretching zone 7, so that the spring rate c is additionally reduced as a result. In addition, it is possible to make or widen the perforation 7 later (not shown).

If excessively strong tensile forces occur in the belt 1 because of the patient's body size, one or more stretching zones 7 may be activated by removing the adhesive tape from the stretching zone 7 in a simple manner (not shown). The stretching zones 7 are stretched substantially more greatly because of the perforations 4 than those of the other areas 3 of the belt 1 without perforations 4, so that the average spring rate c of the belt 1 decreases. The belt 1 can thus be stretched further with a weak tensile force in the belt 1 and it can thus be adapted to the patient's body size. For example, only a tensile force of 2.5 N to 3.5 N (Newton) occurs in the belt 1 in case of a 3% change in the length of the belt 1. The wearing of the belt 1 is therefore pleasant for the patient, because small changes in length due to breathing, motion or tension cause only weak forces.

Figure 7:
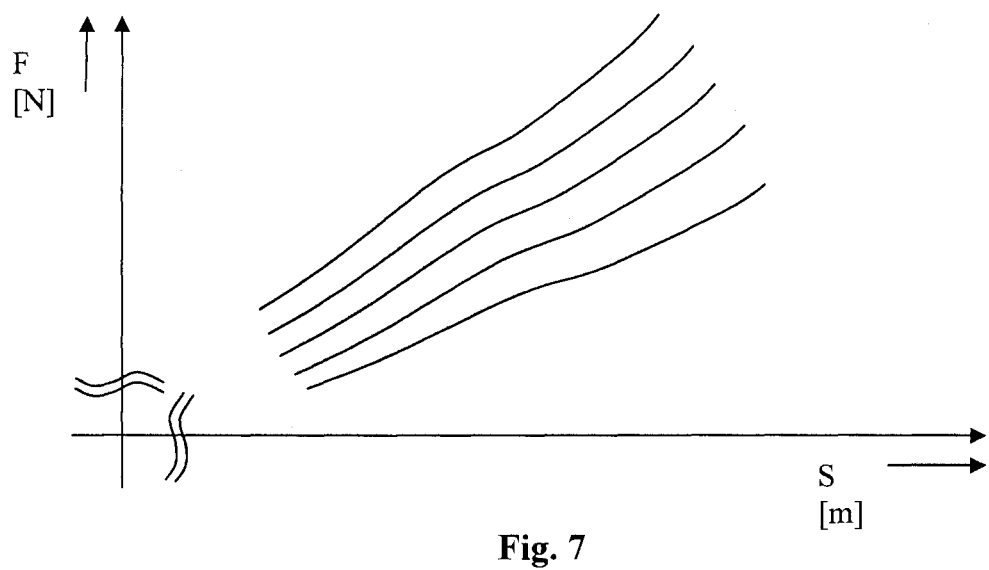
FIG. 7 is a diagram with stretching characteristics of the belt.

FIG. 7 shows a plurality of stretching characteristics of the belt 1. The change in length s is plotted on the abscissa and the force F on the ordinate. The individual stretching characteristics with different slopes show the different average spring rates c of the belt 1 that can be reached, depending on how many stretching zones 7 have been activated by removing the adhesive tape.

On the whole, essential improvements are possible with belt 1. It is not necessary to stock belts 1 of different sizes for adaptation to different body sizes of patients, because the belt 1 can be adapted to the body sizes due to the possibility of activating stretching zones 7. The material neoprene used preferably to manufacture the belt 1 has a very low spring rate c, so that great changes in the length of the belt 1 are also possible as a result of this, without the patients being stressed with strong forces. The belt 1 can thus be additionally adapted to different body sizes. The low and variable average spring rate c of belt 1 makes it possible to achieve a great change in the length of the belt 1 for adaptation to the different body sizes with tensile forces that are comfortable for the patient.

While specific embodiments of the invention have been shown and described in detail to illustrate the application of the principles of the invention, it will be understood that the invention may be embodied otherwise without departing from such principles.

LIST OF REFERENCE NUMBERS

1 Belt
2 Area with lower spring rate
3 Area with higher spring rate
4 Perforation
5 Chest belt
6 Shoulder strap
7 Stretching zones
8 Sensor
9 Closure
10 Electrode
11 Acceleration sensor
12 Temperature sensor
13 $S_pO_2$ sensor

What is claimed is:

1. A stretchable belt for medical purposes for use on the body of a patient, the belt comprising:
   a sensor for detecting at least one parameter of the patient's body;
   stretchable belt material comprising a first material area occupying a first area of a belt material longitudinal extent in a belt longitudinal direction and a second material area occupying a second, different, area of said belt material longitudinal extent in the belt longitudinal direction, said first material area having a lower spring rate of longitudinal extension in the longitudinal direction than said second material area with a higher spring rate of longitudinal extension in the longitudinal direction, wherein the first material area with the lower spring rate is embodied with perforations and/or interruptions of the belt material with the lower spring rate attained by mechanically altering the structure of the belt material through perforations and/or interruptions in the first material area; and
   a blocking means to prevent stretching or allow stretching only slightly of the first material area with the lower spring rate.

2. A stretchable belt in accordance with claim 1, wherein said first material area with the lower spring rate is activated by removing the blocking means.

3. A stretchable belt in accordance with claim 2, wherein the blocking means is an adhesive tape and/or a thread.

* * * * *